United States Patent
Hill et al.

(10) Patent No.: US 9,114,251 B2
(45) Date of Patent: Aug. 25, 2015

(54) MEDICAL IMPLANTABLE LEAD AND A METHOD FOR ATTACHING THE SAME

(75) Inventors: Rolf Hill, Jarfalla (SE); Olof Stegfeldt, Alta (SE)

(73) Assignee: St. Jude Medical AB, Jarfalla (SE)

( * ) Notice: Subject to any disclaimer, the term of this patent is extended or adjusted under 35 U.S.C. 154(b) by 739 days.

(21) Appl. No.: 12/596,607

(22) PCT Filed: Apr. 25, 2008

(86) PCT No.: PCT/SE2008/000292
§ 371 (c)(1),
(2), (4) Date: Oct. 19, 2009

(87) PCT Pub. No.: WO2008/133575
PCT Pub. Date: Nov. 6, 2008

(65) Prior Publication Data
US 2010/0114280 A1    May 6, 2010

Related U.S. Application Data

(60) Provisional application No. 60/913,857, filed on Apr. 25, 2007.

(51) Int. Cl.
*A61N 1/04* (2006.01)
*A61N 1/05* (2006.01)

(52) U.S. Cl.
CPC .................. *A61N 1/0573* (2013.01)

(58) Field of Classification Search
CPC ............................ A61N 1/057; A61N 1/0573
USPC .......................................... 607/116, 122, 127
See application file for complete search history.

(56) References Cited

U.S. PATENT DOCUMENTS

| 4,026,303 | A | 5/1977 | Babotai |
| 5,545,201 | A | 8/1996 | Helland et al. |
| 5,755,764 | A | 5/1998 | Schroeppel |
| 6,687,550 | B1 * | 2/2004 | Doan ............................ 607/127 |
| 6,882,887 | B1 | 4/2005 | Shelchuk et al. |
| 7,212,870 | B1 * | 5/2007 | Helland ........................ 607/127 |
| 2003/0073972 | A1 * | 4/2003 | Rosenman et al. ........... 604/502 |

* cited by examiner

*Primary Examiner* — Christopher D Koharski
*Assistant Examiner* — Michael D Abreu

(57) ABSTRACT

A medical implantable lead of the type being adapted to be implanted into a human or animal body and attached with a distal end to an organ inside the body, has a helix of a helical wire in the distal end which is adapted to be screwed into the organ. In addition to the first helix, the lead also has a second helix of a helical wire, the second helix having the same diameter, the same pitch and being intertwined with the helical wire of the first helix and which, upon rotation of the first helix, will be rotated and screwed into the tissue. The first helix is electrically non-conductive whereas the second helix is electrically conductive. In a method for attaching a medical implantable lead to an organ inside a human or animal body, such a medical lead is employed and fixed to tissue in vivo.

16 Claims, 3 Drawing Sheets

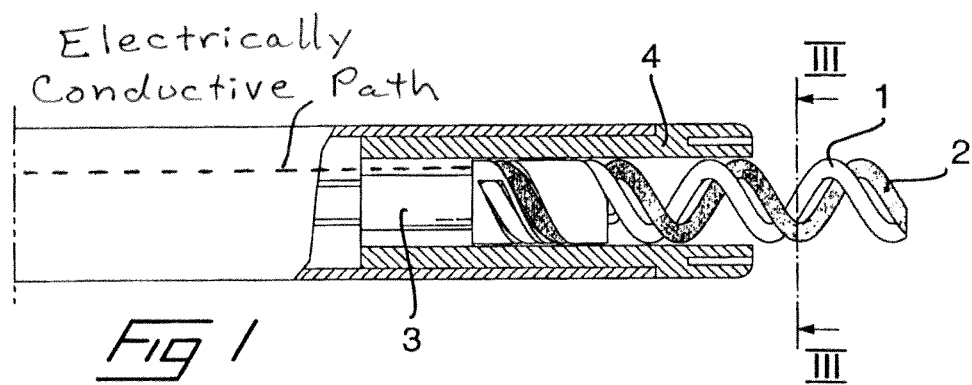
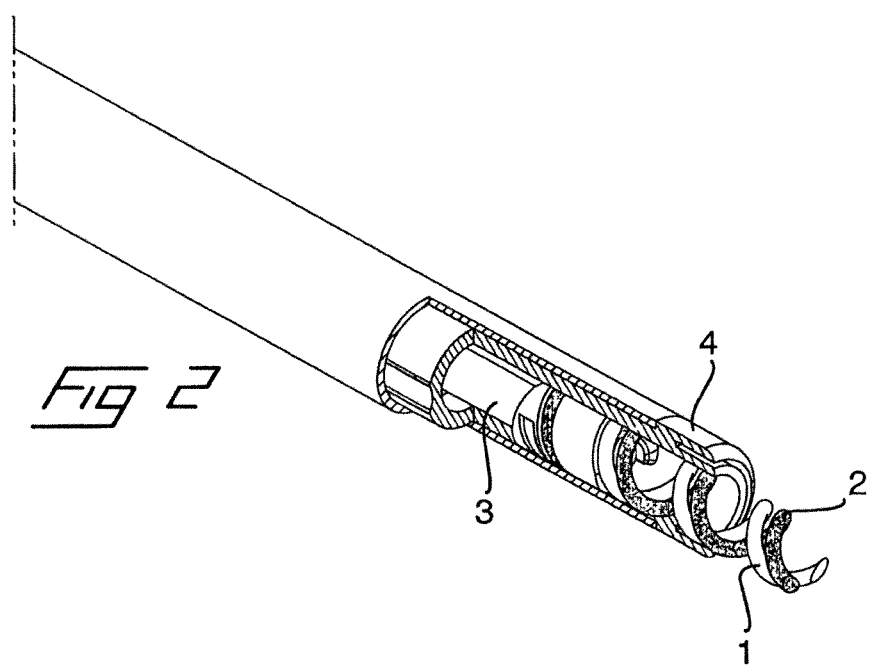
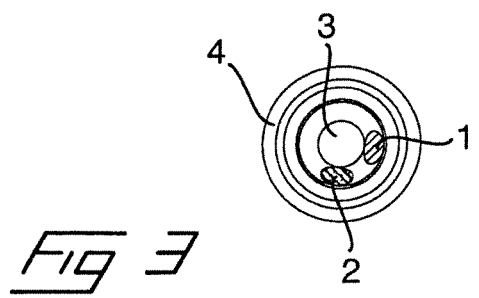

MEDICAL IMPLANTABLE LEAD AND A METHOD FOR ATTACHING THE SAME

BACKGROUND OF THE INVENTION

1. Field of the Invention

The invention relates to a medical implantable lead of the type being adapted to be implanted into a human or animal body and attached with a distal end to an organ inside the body, and having a helix of a helical wire in the distal end which is adapted to be screwed into the organ, wherein the lead, in addition to the first helix, also comprises a second helix of a helical wire, the second helix having the same pitch and being intertwined with the helical wire of the first helix and which, upon rotation of the first helix, will be rotated and screwed into the tissue.

The invention also relates to a method for attaching a medical implantable lead to an organ inside a human or animal body, by screwing a helix of a helical wire into the tissue of the organ.

The invention is primarily adapted for attaching the tip of a cardiac electrode into cardiac tissue for connecting e.g. a pacemaker or defibrillator to a heart. However, the invention is also applicable for attaching other types of electrodes to arbitrary organs in a human or animal body. Accordingly, everywhere in the following description and claims where reference is made to attachment of an electrical lead to a heart, it is to be understood that it may concern also other types of organs where applicable.

2. Description of the Prior Art

Various types of cardiac stimulation devices, such as cardiac pacemakers, have one or more electrode leads connected at one end, commonly called the proximal end, to the implanted stimulator housing, and having an opposite end, commonly called the distal end, which is implanted so as to interact with cardiac tissue. The attachment of the distal end of a cardiac lead to the cardiac tissue is commonly referred to as fixing the lead, or lead fixation.

Typically, the cardiac lead carries an electrode at or near the distal end thereof, and this electrode, by fixing the electrode lead to the cardiac tissue, must be placed in good electrical contact with the cardiac tissue. The distal end of the cardiac lead also must be reliably mechanically affixed to the cardiac tissue, so that beating of the heart, and other physical movements of the subject, will not cause dislodgement of the lead.

Many types of lead fixation techniques and structures are known, one of the most common being to configure the tip electrode of the electrode lead to be in the form of a helix or corkscrew, which is then screwed into the cardiac tissue during the implantation procedure.

An example of such a lead with a helical configuration is described in U.S. Pat. No. 6,687,550. As in the arrangement described in this patent, the helical electrode during implantation is commonly retracted inside of a protective covering or header, and upon reaching the implantation site at the cardiac tissue, the helix is actively caused to protrude from the covering and is screwed into the cardiac tissue.

United States Patent Application Publication No. 2003/0073972 discloses a catheter assembly for implanting a helical fixation device into the myocardium. The catheter assembly has a fixation wire in the form of a helix that is securely fastened to the distal end of the catheter. A drug delivery coil or helix is nested inside the flights (turns) of the fixation helix, but the catheter prevents proximal rotation of the drug delivery coil. When the surgeon screws the fixation coil into the heart wall, the drug delivery helix is driven along with the fixation helix, but when the surgeon unscrews the fixation helix from the heart wall, the drug delivery helix remains in place in the cardiac tissue. The catheter also has a centrally located hollow straight needle that extends through the central axis of the two helices, and is used for penetrating the myocardium when the helices are screwed into the myocardium. The two helices have the same pitch and helix diameter, so as to permit the drug delivery coil to be nested within the fixation helix with a sliding fit.

From U.S. Pat. No. 7,212,870 a helical fixation device is known that has two helices having the same length, diameter and pitch, which are formed of helical wires and are intertwined with each other such that the wires are displaced 180° in relation to each other. The fixation device is adapted to function as a bipolar electrode, wherein one helix will be a cathode whereas the other an anode. One disadvantage with a fixation device like this is that the impedance between each helix and the tissue will be small. A small impedance will lead to increased energy consumption and hence more frequent replacement of the implanted electronic devices due to discharged batteries. In some applications measures may have to be taken to avoid this problem, such as partly insulating of the helices as is disclosed in the document, which will lead to increased costs for manufacturing.

In order to reduce the size of implantable electrode leads, and to reduce the lead impedance, there is a trend to form the fixation helix from thinner wire than in the past, as well as to reduce the outer diameter of the fixation helix. This trend has resulted in side-effects, such as high acute capture thresholds and poor mechanical fixation of the distal end of the lead. It will also lead to an increased risk that the thin wire helix may easily start to rotate in the myocardium behind the endocardium at the surface of the heart wall if the helix is over-rotated. This will tear the myocardium around the helix, which will cause unnecessarily injury to the heart, which causes poor connection, electrically as well as mechanically, and increased capture threshold between the helix and the tissue.

SUMMARY OF THE INVENTION

It is an object of the present invention to provide a fixation arrangement for a medical implantable lead, having a helix, which can be manufactured of a thin wire and with a small helix diameter, but by which the fixating characteristics as well as the electrical connection characteristics can be improved to a low cost.

The invention also relates to a method for attaching a medical implantable lead to an organ inside a human or animal body having essentially the same object as above.

The above object is achieved in accordance with the present invention by a double helix fixation arrangement for a medical implantable lead having two helices, of which one helix is electrically non-conductive whereas the other is electrically conductive. By forming the first helix electrically non-conductive, this helix can be optimally formed for achieving an as good fixation as possible with regard to e.g. its length, cross-sectional dimension of the wire and the like. On the other hand, by forming the second helix electrically conductive, this helix can, in a corresponding way, be optimally formed for achieving an as good electrical connection as possible with regard to e.g. its impedance and capture threshold by varying its length, cross-sectional dimension of the wire and the like. At the same time the helices will interact to provide a more secure fixation to the tissue. In case the helices are arranged on a distance from each other, the fixation arrangement will provide two entry points through the outer layer of the organ, which for most organs has a higher strength in relation to the tissue beneath the outer layer such as for example the outer layer or endocardium of a heart in relation to the underlying myocardium, such that there is provided a protection against over-rotation of the helices and hence destroying of tissue. Over-rotation of a single helix arrangement may occur if the physician performing the implantation, continues to rotate the helix after it has been completely screwed into the tissue and the tip of the lead is abutting the surface of the organ. The helix will then continue to rotate around the entry point in the outer layer and destroy the underlying layer. Due to the double entry points and the comparatively strong outer layer, this risk is considerably reduced. On the other side, in case the helices are arranged without any distance between them, they will act in combination as a flat helical wire with an enlarged width, which will give increased fixation characteristics. By being free to design the second helix in a way for optimally function as an electrode, e.g. by making it shorter, longer, thicker and/or thinner than the first electrode, it is possible to adapt impedance and capture threshold to a desirable level in order to achieve a good electrical contact and restrict the energy consumption.

Within this overall idea, the invention may be realized in many different ways. Normally it is preferred to manufacture the first helix of a metal, which is coated by an electrically insulating material, but it is also possible to manufacture the complete helix of an insulating material such as plastics. However, it could also be possible to manufacture the helix of an electrically conductive material without any insulation if the two helices are held completely separated in relation to each other and there is no risk that they will come into contact with each other during penetration into the tissue. The expression "electrically non-conductive" are accordingly to be interpreted extensively and comprises also the case where the helix is of a metal but non-connected and hence electrically inactive.

There are several ways to control the impedance and the capture threshold of the electrically conducting, second helix. The impedance is normally increased by reducing the overall surface area of the helix, which can be done by reducing the length and/or the cross-sectional dimension of the helical wire. The capture threshold, on the other hand, is lowered if the helix is in good electrical contact with the tissue. When screwing the helix into the tissue, it will be subjected to trauma and the electrical contact will deteriorate within a few days due to the inflammatory process and the subsequent fibrous capsule formation around the helix. Therefore it is normally beneficial to use a helix of a thin helical wire since then the trauma in the tissue will be restricted. It could also in some cases be beneficial if the electrically conductive helix is longer than the electrically non-conductive helix, since then the tip of the electrically conductive helix will be positioned in tissue which is unaffected by the shorter electrically non-conductive helix and might also reach more easily excitable tissue.

The pitch of the first and second helix is the same and is normally at least 1, preferably at least 1.2 and most preferred at least 1.4 mm per winding. The outside diameter of a helix is typically between 1 and 2 mm and preferably around 1.4 mm. The cross-sectional dimension of the helical wire, on the other hand, is normally between 0.25 and 0.35 mm for the fixating, electrically non-conductive helix and between 0.15 and 0.3 mm for the electrically conductive helix.

An advantage that can be achieved if the length of the electrically conducting second helix is made shorter than the first helix, is that the impedance of the electrode can easily be regulated by varying the length of the short helix, whereas the long helix is electrically non-conductive and has a length which is optimal for attaching the lead to the organ in a reliable way. In case the second helix is made shorter than the first helix, normally, the short helix protrudes at least a 30% shorter distance, preferably at least a 40% shorter distance and most preferred at least a 50% shorter distance from the tip of the lead than the long helix.

It is to be understood that the invention may be modified in many different ways. In the hereinafter described and illustrated embodiments of the invention, the helices are rotatable as well as displaceable in relation to the header and the rest of the lead. However, the helices could also be fixed arranged in relation to the lead, in which case the entire lead is rotated when screwing the helices into the tissue. Moreover, the invention could be applicable also in leads where the helices are directed substantially perpendicular in relation to the longitudinal extension of the lead. Although it is preferred, for reducing the manufacturing costs, to let the electrically conductive helix be entirely electrically conductive, it is within the scope of the invention to let the electrically conductive helix be partly insulated, e.g. if it is desirable to have a long helix but be able to increase the impedance. According to the invention, it is however intended that the electrically non-conductive helix is completely electrically inactive.

BRIEF DESCRIPTION OF THE DRAWINGS

FIG. 1 is a side view, partly in section, of the distal end of a medical implantable lead according to a first embodiment of the invention.

FIG. 2 is a perspective view, partly in section of the embodiment of FIG. 1.

FIG. 3 is a cross-section taken along the line III-III in FIG. 1.

DESCRIPTION OF THE PREFERRED EMBODIMENTS

Figure 4:
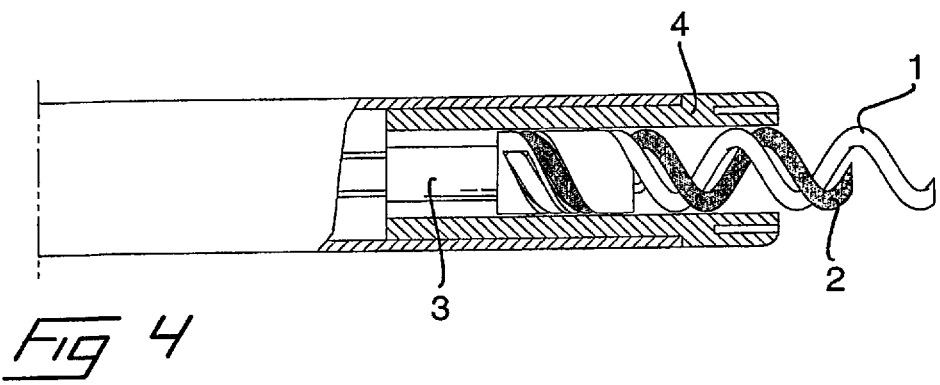
FIG. 4 is a side view, partly in section of the distal end of a medical implantable lead according to a second embodiment of the invention.

In the detailed description given hereinafter, reference is made to use of the medical implantable lead as an electrical lead for connecting a pacemaker or a defibrillator to a heart. It is to be understood however, that the lead can be attached also to other organs in a body.

A first embodiment of an arrangement according to the invention is shown in FIGS. 1-3. In accordance with the present invention, a dual helix fixation arrangement has two fixation helices 1, 2, each formed of a helical wire and each terminating in a sharp point that is capable of penetrating the endocardium and the myocardium of a heart.

The two helices are mounted in a holder portion on a shaft 3 that can be rotated from the opposite, proximal end of the lead or the implantation device by means of for example a rotatable coil or a stylet in a way commonly known in the art. When the shaft 3 and the two helices 1, 2 are rotated, this causes them to advance from inside a protective covering or header 4, in which they are initially positioned, so as to penetrate into the endocardium and the myocardium. In the illustrated embodiment the two helices have the same diameter and pitch but are displaced by about 90° in relation to each other, as is best seen in FIG. 3, in order to position the helical wires with a small distance from each other. In order to restrict the impedance, the first helix 1 is insulated and hence electrically non-conductive, whereas the second helix 2 is uninsulated and hence electrically conductive for signals to or from the tissue.

As schematically indicated in FIG. 1, the second helix 2 forms an electrically conductive path, together with a conductor within the lead body, which proceeds from the proximal end of the lead body to the distal end, allowing delivery of electrical energy to an organ via the second helix 2.

Figure 5:
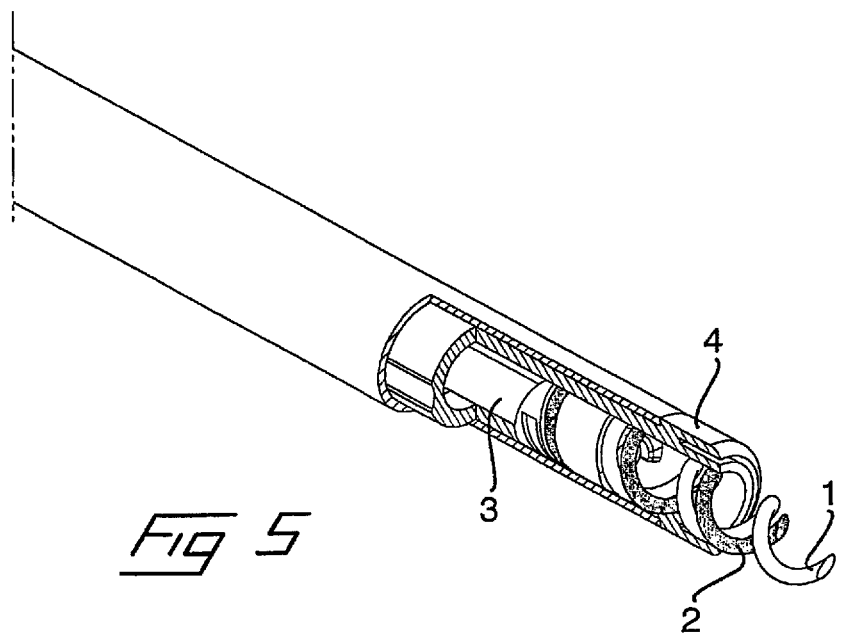
FIG. 5 is a perspective view, partly in section, of the embodiment of FIG. 4.

Thereafter reference is made to FIGS. 4 and 5, in which is illustrated a second embodiment of the invention. Here, the helical wires of the first and second helices 1, 2 have the same diameter and they are positioned with the same distance from each other, i.e. displaced about 90° in relation to each other, as in the first embodiment. In order to adjust the impedance, the uninsulated second helix 2 is made shorter than the insulated first helix 1. In this way the impedance of the second helix is increased and by adjusting the length of the short, second helix, the impedance can easily be regulated to a desired level.

Figure 6:
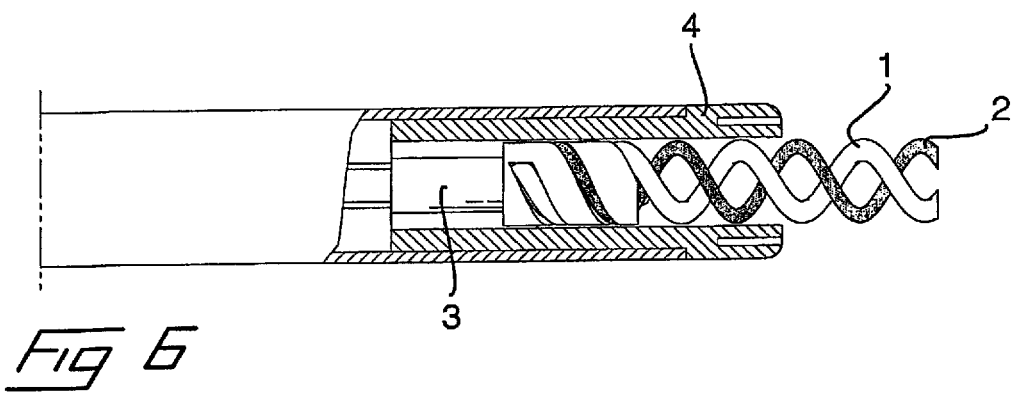
FIG. 6 is a side view, partly in section, through the distal end of a medical implantable lead according to a third embodiment of the invention.
Figure 7:
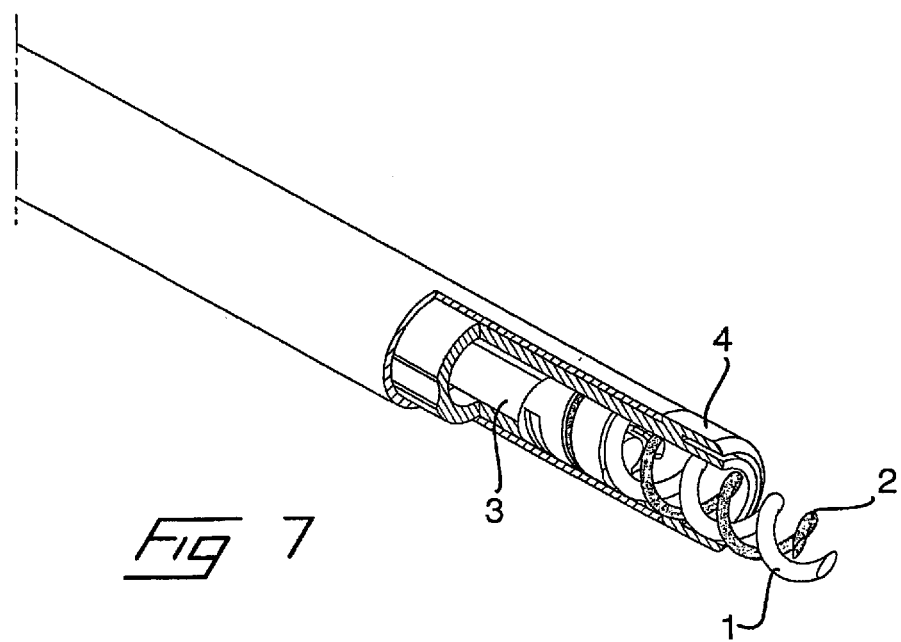
FIG. 7 is a perspective view, partly in section, of the embodiment of FIG. 6.

In FIGS. 6 and 7 is disclosed a third embodiment of the invention. Here the first and second helices 1, 2 have the same length and are displaced 180° in relation to each other. However, in order to increase the impedance of the second helix 2, it has been manufactured of a thinner wire than the first helix 1. Accordingly, the first helix 1 can be formed of a helical wire of a desirable cross-sectional dimension to achieve an optimal fixation to the tissue, whereas the second helix 2 can be formed of a helical wire of a desirable cross-sectional dimension to achieve an optimal electrical connection to the tissue with respect to e.g. impedance and capture threshold.

Since the dual helices of all three of the embodiments described above are mounted with a distance in relation to each other, over-rotating of the header/helix combination is prevented when torque is applied to the helix during implantation. This is due to the fact that by using dual helices with a proper pitch, two entry punctures are made in the strong endocardium, which will prevent the helix from over-rotating in and thereby damaging the softer myocardium. With two entry points through the endocardium, the entire endocardium would in that case have to be twisted around the header, which does not normally occur. This allows the helices to be made of thinner wire and also allows helices of smaller diameter to be used, thereby allowing the overall lead to be of a smaller diameter.

It is also to be understood that a medical implantable lead according to the invention, can be formed as a combination of the embodiments described above. E.g. as a medical implantable lead having a second helix, which is thinner as well as shorter than the first helix and the helices can be displaced in arbitrary angles in relation to each other.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical implantable lead comprising:
   a lead body configured for in vivo implantation in a living subject, said lead body having a proximal end and an opposite, distal end, said lead body comprising an electrical conductor therein proceeding from said proximal end to said distal end;
   a rotatable shaft proceeding through said proximal end of said lead body to said distal end of said lead body;
   a first fixation helix formed by a first helical wire located at said distal end of said lead body, said first helical wire having a proximal end directly attached to a distal end of said rotatable shaft such that said first fixation helix being rotationally mounted at said distal end and comprising helical flights configured to screw said first fixation helix into an organ of the living subject upon rotation of said first fixation helix to fix and hold said first fixation helix in said organ; and
   a second fixation helix formed by a second helical wire also located at said distal end of said lead body, said second helical wire having a proximal end directly attached to said distal end of said rotatable shaft such that said second fixation helix comprising helical flights having a same pitch as said helical flights of said first fixation helix and being mounted at said distal end intertwined with said first fixation helix to cause co-rotation of said second fixation helix with said first fixation helix to screw said second fixation helix into said organ to fix and hold said second fixation helix in said organ;
   said first helical wire and said second helical wire arranged without any distance between them such that said first helical wire and said second helical wire act in combination as a single helical wire; and
   said first helical wire forming said first fixation helix being electrically non-conductive and said second helical wire forming said second fixation helix being electrically conductive and forming an electrically conductive path with said electrical conductor in said lead body to deliver electrical energy to said organ via said second helical wire serving as an electrode that electrically interacts with said organ, and said first and second fixation helices holding said electrode in place at said organ during delivery of said electrical energy.

2. A medical implantable lead as claimed in claim 1 wherein said second fixation helix has a length that is shorter than a length of said first fixation helix.

3. A medical implantable lead as claimed in claim 2 wherein said lead body terminates at a tip at said distal end, and wherein said second fixation helix, after said co-rotation with said first fixation helix, protrudes from said tip by a distance that is at least 30% less than a distance that said first fixation helix protrudes from said tip after said co-rotation.

4. A medical implantable lead as claimed in claim 2 wherein said lead body terminates at a tip at said distal end, and wherein said second fixation helix, after said co-rotation with said first fixation helix, protrudes from said tip by a distance that is at least 40% less than a distance that said first fixation helix protrudes from said tip after said co-rotation.

5. A medical implantable lead as claimed in claim 2 wherein said lead body terminates at a tip at said distal end, and wherein said second fixation helix, after said co-rotation with said first fixation helix, protrudes from said tip by a distance that is at least 50% less than a distance that said first fixation helix protrudes from said tip after said co-rotation.

6. A medical implantable lead as claimed in claim 1 wherein said first fixation helix and said second fixation helix have the same diameter.

7. A medical implantable lead as claimed in claim 1 wherein said second helical wire forming said second fixation helix is thinner than said first helical wire forming said first fixation helix.

8. A medical implantable lead as claimed in claim 1 wherein the respective flights of the first fixation helix and the second fixation helix are not rotationally offset by an angle at said distal end.

9. A medical implantable lead as claimed in claim 1 wherein each of said first fixation helix and said second fixation helix is comprised of flights, and wherein said first fixation helix and said second fixation helix are positioned at said distal end with the respective flights of the first fixation helix and the second fixation helix adjacent each other.

10. A medical implantable lead as claimed in claim 1 wherein each of said first fixation helix and said second fixation helix is comprised of flights, and wherein each of said first fixation helix and said second fixation helix has a pitch that is at least one 1.0 mm per flight.

11. A medical implantable lead as claimed in claim 1 wherein each of said first fixation helix and said second fixation helix is comprised of flights, and wherein each of said first fixation helix and said second fixation helix has a pitch that is at least one 1.2 mm per flight.

12. A medical implantable lead as claimed in claim 1 wherein each of said first fixation helix and said second fixation helix is comprised of flights, and wherein each of said first fixation helix and said second fixation helix has a pitch that is at least one 1.4 mm per flight.

13. A medical implantable lead as claimed in claim 1 wherein said lead body comprises a header sleeve located at said distal end.

14. A medical implantable lead as claimed in claim 1 wherein said first fixation helix is electrically insulated, and wherein said second fixation helix is uninsulated.

15. A method for attaching a medical implantable lead to an organ inside a living subject in order to deliver electrical energy to the organ, comprising:

implanting a medical lead, having a lead body with a distal end, in a living subject to cause said distal end of said lead body to be located adjacent to an organ to which the medical lead is to be affixed, said lead body comprising an electrical conductor therein proceeding from a proximal end to said distal end;

from said lead body, simultaneously rotationally advancing a first fixation helix and a second fixation helix from said distal end of said lead body to screw each of said first fixation helix and said second fixation helix into said organ, proximal ends of said first fixation helix and said second fixation helix directly attached to a rotatable shaft;

arranging said first fixation helix and said second fixation helix without any distance between them such that said first fixation helix and said second fixation helix act in combination as a single helical wire; and forming said first fixation helix of material designed to optimally mechanically fix said first fixation helix to said organ without electrically stimulating said organ, and forming said second fixation helix of material designed for optimal electrical stimulation of the organ; and delivering electrical energy to said organ via a conductive path that comprises said electrical conductor in said lead body and said second fixation helix, with said second fixation helix serving as an electrode, while holding said distal end of said lead body adjacent to said organ with said first fixation helix and said second fixation helix.

16. A method as claimed in claim 15 comprising making said first fixation helix non-electrically conductive with respect to said organ by insulating said first fixation helix, and making said second fixation helix electrically conductive with respect to said organ by maintaining said second fixation helix uninsulated.

* * * * *